United States Patent
Bewig et al.

(10) Patent No.: US 9,619,619 B2
(45) Date of Patent: Apr. 11, 2017

(54) METHOD FOR ERROR RECOGNITION IN A CONTROL SYSTEM OF A MEDICAL TREATMENT AND/OR DIAGNOSIS DEVICE

(75) Inventors: Lorenz Bewig, Freising (DE); Till Engelmann, Erlangen (DE); Andreas Hagenauer, Friedberg (DE); Torsten Hasenzahl, Dillingen (DE); Dirk Jacob, Augsburg (DE); Matthias Mühlhäusser, Herzogenaurach (DE); Tobias Ortmaier, Hemmingen (DE); Dietmar Tscharnuter, Friedberg (DE)

(73) Assignees: Siemens Aktiengesellschaft, München (DE); KUKA Roboter GmbH, Augsburg (DE)

( * ) Notice: Subject to any disclaimer, the term of this patent is extended or adjusted under 35 U.S.C. 154(b) by 632 days.

(21) Appl. No.: 12/811,508

(22) PCT Filed: Dec. 15, 2008

(86) PCT No.: PCT/EP2008/067496
§ 371 (c)(1),
(2), (4) Date: Oct. 12, 2010

(87) PCT Pub. No.: WO2009/087017
PCT Pub. Date: Jul. 16, 2009

(65) Prior Publication Data
US 2011/0022407 A1    Jan. 27, 2011

(30) Foreign Application Priority Data
Jan. 7, 2008    (DE) .......................... 10 2008 003 440

(51) Int. Cl.
*G06F 19/00*    (2011.01)
*G06Q 50/22*    (2012.01)

(52) U.S. Cl.
CPC ......... *G06F 19/3406* (2013.01); *G06Q 50/22* (2013.01)

(58) Field of Classification Search
CPC ... G06N 3/008; B25J 9/161; B25J 9/02; B25J 9/06; B25J 9/023; B25J 9/10;
(Continued)

(56) References Cited

U.S. PATENT DOCUMENTS 4,831,549 A * 5/1989 Red .................. B25J 9/1692
                                                  700/254
5,862,502 A * 1/1999 Giers .................. B60T 8/885
                                                  303/122
(Continued)

FOREIGN PATENT DOCUMENTS

CN        1471626 A    1/2004
CN        1892662 A    1/2007
(Continued)

OTHER PUBLICATIONS

German Office Action dated Dec. 19, 2008 for corresponding German Patent Application No. DE 10 2008 003 440.1 with English translation.
(Continued)

*Primary Examiner* — Elaine Gort
*Assistant Examiner* — Jason Tiedeman
(74) *Attorney, Agent, or Firm* — Lempia Summerfield Katz LLC

(57) ABSTRACT

A method for error recognition in a control system of a medical treatment and/or diagnosis device includes processing, by the control system, data in a regular operating mode and supplying, by the control system, test data of a test data record to a safety-critical component of the control system
(Continued)

in a test mode of the control system. The safety-critical component of the control system is also checked in the test mode of the control system.

21 Claims, 1 Drawing Sheet

(58) Field of Classification Search
CPC . B25J 9/1005; B25J 9/16; B25J 9/1628; B25J 9/163; B25J 9/1653; B25J 9/1674; G06Q 50/22; G06Q 50/24; G06F 19/322; G06F 19/323–19/327; G06F 19/3406
USPC ......... 705/2, 1.1–3; 700/245, 250, 254, 262; 901/2, 8, 9
See application file for complete search history.

(56) References Cited

U.S. PATENT DOCUMENTS

| | | | | |
|---|---|---|---|---|
| 6,033,415 | A * | 3/2000 | Mittelstadt et al. | 606/130 |
| 6,519,860 | B1 * | 2/2003 | Bieg | G01B 5/008 33/1 PT |
| 6,577,918 | B1 * | 6/2003 | Roth | 700/177 |
| 6,614,038 | B1 * | 9/2003 | Brand et al. | 250/492.3 |
| 6,937,943 | B2 * | 8/2005 | Budmiger | 702/45 |
| 7,114,157 | B2 * | 9/2006 | Chaffee et al. | 718/104 |
| 7,747,406 | B2 | 6/2010 | Böing et al. | |
| 7,930,065 | B2 * | 4/2011 | Larkin | A61B 19/2203 600/104 |
| 8,065,060 | B2 * | 11/2011 | Danko | B25J 9/1628 700/11 |
| 2003/0144809 | A1 * | 7/2003 | Puchtler | G05B 19/404 702/105 |
| 2004/0267404 | A1 * | 12/2004 | Danko | B25J 9/1607 700/245 |
| 2006/0074527 | A1 * | 4/2006 | Bhatt | B25J 9/1658 700/251 |
| 2007/0050759 | A1 * | 3/2007 | Boing et al. | 717/135 |
| 2007/0078565 | A1 * | 4/2007 | Ghodoussi et al. | 700/245 |
| 2007/0195922 | A1 * | 8/2007 | Mackie et al. | 378/4 |
| 2009/0069936 | A1 * | 3/2009 | Kock | B23K 11/318 700/254 |
| 2010/0145521 | A1 * | 6/2010 | Prisco | A61B 1/00193 700/264 |
| 2010/0299101 | A1 * | 11/2010 | Shimada | G09B 23/28 702/150 |
| 2011/0022407 | A1 * | 1/2011 | Bewig et al. | 705/2 |

FOREIGN PATENT DOCUMENTS

| | | |
|---|---|---|
| DE | 19907771 A1 | 8/2000 |
| EP | 1113760 B1 | 11/2008 |
| JP | 3071983 A | 3/1991 |
| JP | 8141950 A | 6/1996 |
| KR | 1019950003978 | 4/1995 |

OTHER PUBLICATIONS

PCT Search Report/Written Opinion of the International Searching Authority dated May 8, 2009 for corresponding PCT Appl. No. PCT/EP2008/067496 with English translation.

Chinese Office Action dated Apr. 23, 2012 for corresponding Chinese Patent Application No. 200880124212.3 with German translation and English translation of the German translation.

Chinese Office Action dated Jan. 22, 2013 for corresponding Chinese Patent Application No. 200880124212.3 with English translation.

* cited by examiner

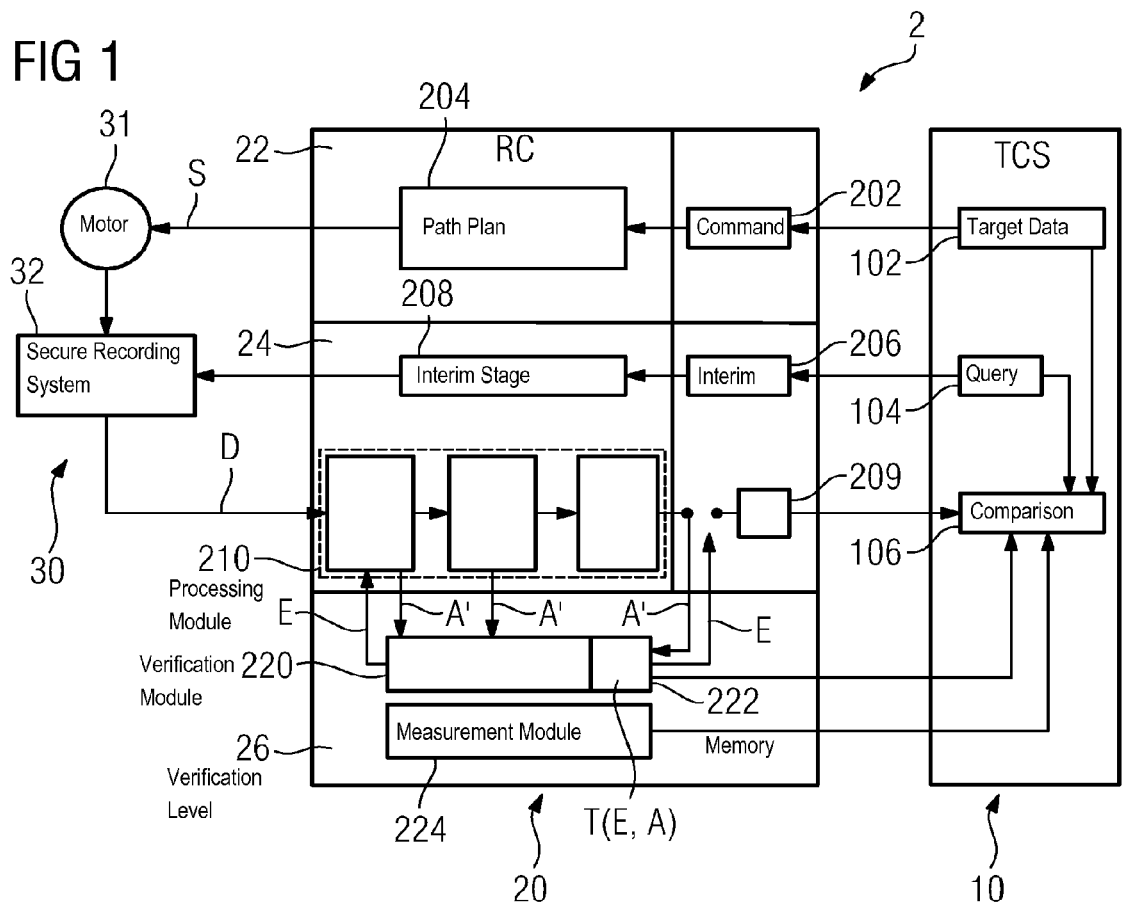
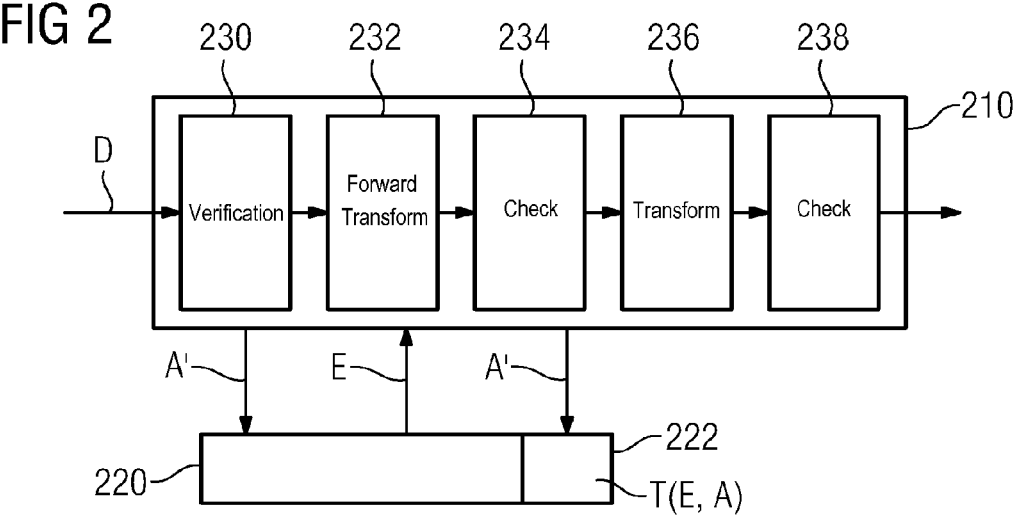

METHOD FOR ERROR RECOGNITION IN A CONTROL SYSTEM OF A MEDICAL TREATMENT AND/OR DIAGNOSIS DEVICE

The present patent document is a §371 nationalization of PCT Application Serial Number PCT/EP2008/067496, filed on Dec. 15, 2008, designating the United States, which is hereby incorporated by reference. This patent document also claims the benefit of DE 10 2008 003 440.1, filed Jan. 7, 2008, which is also hereby incorporated by reference.

BACKGROUND

The present embodiments relate to a method for error recognition in a control system of a medical treatment and/or diagnosis device.

Program-controlled treatment and/or diagnosis devices are used in many applications in modern diagnostics and therapeutics. Because of the sometimes complex sequence of control and movement steps, these devices may also be known as robots (e.g., as control systems are used that are largely similar to those used in industrial robot applications). The use of such robots in safety-critical applications such as, for example, medical engineering, places very high demands on system safety. It must be possible that any malfunction in the robot can be detected and that the robot can be transferred to a safe condition in the event of a malfunction of the robot. A safe condition may stop the robot, for example. For this purpose, the correct functioning of critical hardware and software components are checked during operation and any malfunction detected.

To achieve this, safety-critical components may be redundantly designed. Output values are also checked continuously against target values so that, if there is any deviation, it may be concluded that a fault has occurred in one of the safety-critical components. Appropriate measures may then be taken to transfer the system to a safe condition. These embodiments of robot systems have a very high processing requirement. The result for critical software components, in particular, is an increased resource requirement in terms of processing time and memory space. In addition, independence of redundant components from one another may be regarded as disadvantageous. This applies equally for functions that lead to additional hardware costs.

SUMMARY AND DESCRIPTION

The present embodiments may obviate one or more of the drawbacks or limitations in the related art. For example, in one embodiment, an improved method for recognizing and/or avoiding errors in a control system is provided.

The method includes an operating mode, in which real data is processed, and a test mode, in which a safety-critical component of a control system is supplied with test data of a test data record. The safety-critical component is also checked by the test data of the test data record. A test run is carried out with the test data in order to check the safety-critical component of the control system. The safety-critical component is, for example, a single-channel non-redundant component. The control system includes a control program that is designed for implementing the acts described herein.

The method is used for recognizing and/or eliminating errors in control systems of medical treatment and/or diagnosis devices. Specifically, the method may be used for recognizing errors, eliminating errors, or recognizing and eliminating errors in control systems of motorized adjustment systems of such devices (e.g., a robot system, with which a treatment unit, a diagnostic unit, or a patient couch is transferred to a defined target position). The regular operating mode is an operating mode in which an actual, real adjustment of the adjustment system is carried out. The test mode is an operating mode in which only test data stored in a memory, which corresponds to potential real values, is processed by the control system, and the output values thus generated are checked. The output data determined in test mode are compared with target values (e.g., reference data). The reference data is stored test data. If the output data determined in test mode deviates from the stored test data by predefined values, a programming error and/or device fault may be recognized in this manner.

The present embodiments thus avoid a redundant execution of critical components with the disadvantages described above. A verification of the correct functioning of the program sequences is possible cyclically and/or acyclically during operation or prior to commissioning.

The present embodiments enable random errors (e.g. buffer overflow and inversion of bits) to be detected.

The test data record advantageously contains, as test data, pairs of values (e.g., input values) that may occur as data in real operation and assigned output values as reference data. The assigned output values are generated by the safety-critical component in correct operating mode. In test mode, the component is supplied with an input value in each case, and the output value calculated by the component is compared with the respective output value corresponding to the input value and stored in the test data record. Real operation is therefore simulated with the test mode, and any deviation of the computed data from the stored data that is expected is a fault.

In operating mode, the data processed by the component is positioning data of an adjustment system, which are processed by the control system and transferred to a medical control system for a target/actual comparison. A safety-critical calculation of positioning data is therefore checked in test mode to prevent the medical control system from outputting incorrectly calculated ACTUAL data. Incorrectly outputted calculated ACTUAL data may cause the medical control system to issue incorrect control commands to the robot control and may prevent a highly accurate positioning operation of, for example, the patient or a therapeutic or diagnostic unit (e.g., an x-ray source) from being carried out. Incorrectly outputted calculated ACTUAL data may also cause a failure to detect incorrect positioning by the medical control system.

The safety-critical component to be checked is a processing module, in which the positioning data on the input side is subjected to a coordinate transformation process. The adjustment system may be a multi-axis (industrial) robot. Adjustment motors of the multi-axis robot are controlled by the control system (e.g., the robot control). The robot control may expect axis-specific coordinates from the adjustment system. However, Cartesian positioning data is regularly provided by the medical control system. The axis-specific coordinates are therefore transformed within the robot control into Cartesian coordinates in a forward transformation. The transformation takes place in the safety-critical component.

The test data record for the component to be monitored is advantageously generated before the system is commissioned for the first time in operating mode. Before the safety-critical function is called up for the first time with the "real" data, the correct functioning is checked using the test data record. Alternatively or in addition, the test data record is generated during a correct operating mode of the device.

In one embodiment, correct test data or a test data record is read in from an external source.

The test mode may be recurrent. For example, the test mode is carried out several times in succession and/or at cyclic intervals, so that the system is continuously being checked. This has the advantage that all relevant paths of the safety-critical component are implemented at least once. The test mode is advantageously carried out far more frequently than the real operating mode.

The test mode may be executed by adjustment to the processing power available, for example, cyclically and/or acyclically. This prevents the real operation from being slowed down or disrupted by the test mode.

The results calculated with the input data are compared with the stored output values. Any deviation above a threshold value is concluded to be due to a malfunction of the safety-critical component. In one embodiment, if an error is detected, a warning signal may be generated and/or the device may be transferred to a safe condition. A further signal may also be generated that may be stored and used for evaluation of the type and/or frequency of the error that has occurred.

In one embodiment of the method, the test data has erroneous values defined for the test mode. In this way, the test method may also be subjected to checking, since the detection of an error may likewise be checked. This act is therefore used for checking the functionality of the error detection of the system.

In one embodiment, a medical treatment and/or diagnosis device is provided. The advantages and embodiments relating to the method may also be transferred analogously to the device.

Further features of the present embodiments are described below in the detailed description. The detailed description is used as a nonrestrictive example and makes reference to the attached drawings.

BRIEF DESCRIPTION OF THE DRAWINGS

FIG. 1 shows a block diagram of a method for the control of a medical diagnosis or treatment device; and FIG. 2 shows a block diagram of a subsection of a control system.

DETAILED DESCRIPTION OF THE DRAWINGS

An embodiment of a method for error recognition in a medical device 2 is illustrated in FIGS. 1 and 2. In one embodiment, the method is used for reliable verification of the accurate position of an accurately measured robot. In this application, a safety-critical function to be monitored is the accurate robot model calculated on the basis of robot control.

For highly accurate positioning with currently known controls, the position of a machine or robot may be verified by an additional measurement system. The additional measurement system may reliably verify whether the robot also occupies the position that has been provided for the robot by the control. In the case of an accurate machine, the accurate position arrived at may be verified with the additional measuring system such as, for example, a laser tracker or a coordinate measuring machine. The described method helps an accurate robot arrive safely at an accurate position without the additional measuring system. Therefore, costs may be considerably reduced. One embodiment for an actual implementation is illustrated by the flow charts in FIGS. 1 and 2.

The method for verifying the position to be arrived at is also known as a "health check", which is the correct functioning and thereby the "health" of the safety-critical component to be monitored. The health check therefore constitutes a monitoring function.

In the block diagram shown in FIG. 1, the right-hand block labeled "TCS" (Therapy Control System) indicates the part for the control of the medical device 2 (e.g., a medical control system 10). This provides, for example, the movement data for a computed tomography examination and also checks the movement data.

The larger central block labeled "RC" (Robot Control) indicates the section for the actual robotic control (e.g., a control system 20) and therefore, the area closer to the machine. With this control, an actual adjustment system 30, in particular adjustment motors 31 of the robot, is controlled.

With the help of target data 102 predefined by the medical control system 10, drive commands 202 are generated by the control system 20 and further processed after implementation of a path plan 204 in order to generate control signals S for the motors 31. The target data 102, which may be predefined as Cartesian coordinates, is transformed in a backward transformation into axis-specific coordinates (e.g., multi-axis) of the robot. This area of the control system 20 is also known as the regulating channel 22.

The control system 10 carries out a query 104 to obtain a current, up-to-date actual position of the adjustment system 30, which is processed in a monitoring channel 24 of the control system 20 in interim stages 206, 208. The current, up-to-date actual position of the adjustment is transferred to a secure recording system 32 of the adjustment system 30, where each query is assigned a sequential number as a unique identifier.

The secure recording system 32, depending on type, delivers a response to the query of a large quantity of data D relating to the current status of the adjustment system 30 (e.g., the current positions) to the control system 20.

The data D is, for example, axis-specific positioning data of the individual robot axes for the current ACTUAL positions of individual robot parts or robot axes, corresponding Cartesian coordinates according to a stored standard model, and also checksums. The consistency or plausibility of the data D, for example, may be checked on the basis of the checksums. The current actual data is labeled with the relevant sequential number.

In a processing module 210 of the monitoring channel 24, the edited data may be computationally processed, and the processed data is transferred, if appropriate, via a buffer 209, to a comparison module 106 of the control system 10. In the comparison module 106, the ACTUAL data is compared with the previously defined TARGET data. The processing module 210 may be part of a robot control or of a medical device, or may be a component thereof.

The processing of the edited data in the processing module 210 is safety-critical, since the processing is non-redundant and designed to be single-channel only. In order to check the safety-critical processing, the functioning of the processing module 210 is checked in a verification level 26 of the control system 20 as part of a "health check" in a verification module 220. A test data record T(E,A) is stored in a memory 222 in a table for the "health check." The test data record T (E, A) is generated before the first commissioning of the real operation and contains pairs of values (e.g., input values (E) and output values (A) to be expected for the processing module 210) as test data.

A measurement module 224 is provided in the verification level 26 and forwards key data to the control system 10 for the TARGET/ACTUAL comparison. The key data is, for example, the motor currents of the individual motors 31 for the respective robot axes, load data (e.g., the weight of a patient who is situated on a couch moved by the adjustment mechanism), or tool data (e.g., data relating to deflection and torsion etc).

The implementation of a test mode with the help of the verification module 220 is described in greater detail below with the help of FIG. 2.

The processing of the data D in the processing module 210 takes place in a number of acts 230-238. In act 230, a checksum verification is carried out in order to check the consistency of the data (D). In act 232, the highly accurate, forward transformation of the axis-specific coordinates into Cartesian coordinates is carried out. In act 234, the Cartesian coordinates are subjected to a plausibility check by comparing the Cartesian coordinates with the Cartesian coordinates delivered by the secure recording system 32. In act 236, a transformation of the coordinates is carried out according to a standard, on the basis of which the control system 10 operates. In act 238, a check or checksum creation is carried out for a consistency check or plausibility check, in order to make the data safe.

In order to implement the test mode, the verification module 220 supplies the processing module 210 with input values E and reads the respective output values A' that are calculated. The verification module 220 checks the calculated output values A' on the basis of a comparison with the output values A stored in the memory 222.

The test mode may be implemented before a first real operating mode, as well as during the operating mode or in between consecutive operating modes, in which a real control of the adjustment mechanism 30 is carried out. The functionality of the safety-critical processing module 210 is monitored by cyclic or permanent comparison via the verification module 220. The test mode may be carried out during periods of low processor utilization, in order to make best possible use of available processor capacity and to avoid disrupting the normal operating mode.

If an error is detected by the verification module 220, then the adjustment system 30 is transferred to a safe condition.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method for error recognition and correction in a control system of a medical treatment, diagnosis, or medical treatment and diagnosis device, the medical treatment, diagnosis, or medical treatment and diagnosis device comprising a robot system, the robot system comprising a control motor, the method comprising:
operating the medical treatment, diagnosis, or medical treatment and diagnosis device in a regular operating mode;
processing data in the regular operating mode;
instantiating a test mode of the control system, the test mode simulating real operation of the regular operating mode, the simulating comprising:
supplying a safety-critical component of the control system with test data of a test data record, the test data comprising pairs of previously determined values, the pairs of previously determined values comprising an input value that is occurrable as data in actual operation of the safety-critical component and a corresponding expected output value generated by the safety-critical component operating in correct operating mode in response to the input value, the input value and expected output value comprising positioning data;
checking, using a processor of the control system, the safety-critical component in the test mode, the checking comprising:
calculating a test output value based on the input value, the calculating comprising:
checking consistency of the input value, checking the consistency of the input value comprising carrying out a checksum verification, the input value comprising axis-specific coordinates;
performing a forward transformation of the axis-specific coordinates into Cartesian coordinates;
conducting a first plausibility check, the conducting of the first plausibility check comprising comparing the Cartesian coordinates with predetermined Cartesian coordinates; and
performing a consistency check or a second plausibility check of the transformed Cartesian coordinates, the performing of the consistency check or the second plausibility check comprising performing a check or checksum; and
comparing the test output value calculated in the test mode with the expected output value generated by the safety-critical component during the correct operating mode;
determining a deviation between the test output value and the expected output value determined in the test mode and determining whether the deviation exceeds a threshold; and
correcting the regular operating mode, the correcting comprising adjusting the operation of the control motor of the robot system based on the deviation when the deviation exceeds the threshold.

2. The method as claimed in claim 1, wherein the data in the regular operating mode is real positioning data of the medical treatment device, the diagnosis device or the medical treatment and diagnosis device, and
wherein the method further comprises:
processing, by the control system, the real positioning data;
transferring the real positioning data to a medical control system; and
TARGET/ACTUAL comparing the processed real positioning data at the medical control system.

3. The method as claimed in claim 2, wherein the safety-critical component is a processing module, in which input-side positioning data is subjected to a coordinate transformation.

4. The method as claimed in claim 2, wherein the test data record is generated during the correct operating mode of the medical treatment device, the diagnosis device, or the medical treatment and diagnosis device or is provided from an external source.

5. The method as claimed in claim 4, further comprising generating a warning signal, transferring the medical treatment device, the diagnosis device, or the medical treatment and diagnosis device to a safe condition or generating the warning signal and transferring the medical treatment device, the diagnosis devices, or the medical treatment and diagnosis device to the safe condition when the malfunction is detected.

6. The method as claimed in claim 2, wherein the test mode is carried out recurrently.

7. The method as claimed in claim 2, wherein the test data has defined erroneous values for the test mode for checking the functionality of the error recognition.

8. The method as claimed in claim 2, wherein the test data record is generated during the correct operating mode of the medical treatment device, the diagnosis device, or the medical treatment and diagnosis device or is provided from an external source.

9. The method as claimed in claim 2, wherein the test mode is carried out recurrently.

10. The method as claimed in claim 1, wherein the test data record is generated during the correct operating mode of the medical treatment device, the diagnosis device, or the medical treatment and diagnosis device or is provided from an external source.

11. The method as claimed in claim 1, wherein the test mode is carried out recurrently.

12. The method as claimed in claim 11, wherein the test mode is executed by adjusting the test mode to free and currently available processing power.

13. The method as claimed in claim 1, further comprising detecting a malfunction when the test output value calculated in the test mode deviates from the expected output value of the test data record.

14. The method as claimed in claim 13, further comprising generating a warning signal, transferring the medical treatment device, the diagnosis device, or the medical treatment and diagnosis device to a safe condition or generating the warning signal and transferring the medical treatment device, the diagnosis device, or the medical treatment and diagnosis device to the safe condition when the malfunction is detected.

15. The method as claimed in claim 1, wherein the test data has defined erroneous values for the test mode for checking the functionality of the error recognition.

16. The method as claimed in claim 1, wherein the control system is a control system for an adjustment system of the medical treatment device, the diagnosis device or the medical treatment and diagnosis device.

17. The method as claimed in claim 16, wherein the data in the regular operating mode is real positioning data of the adjustment system, and
wherein the method further comprises:
processing, by the control system, the real positioning data;
transferring the real positioning data to a medical control system; and
TARGET/ACTUAL comparing the processed real positioning data at the medical control system.

18. The method as claimed in claim 17, further comprising detecting a malfunction when the test output value calculated in the test mode deviates from the expected output value of the test data record.

19. The method as claimed in claim 1, further comprising transferring a motor of the medical treatment, diagnosis, or medical treatment and diagnosis device into a safe condition based on the comparing.

20. A program-controlled medical treatment, diagnosis, or medical treatment and diagnosis device comprising:
an adjustment system comprising a robot system, the robot system comprising a control motor; and
a control system configured for error recognition and correction, the control system comprising a processor configured to:
process data in a regular operating mode;
instantiate a test mode of the control system, the test mode simulating real operation of the regular operating mode, the simulation comprising:
supply of a safety-critical component of the control system with test data of a test data record, the test data comprising pairs of previously determined values, the pairs of previously determined values comprising an input value that is occurrable as data in actual operation of the safety-critical component and a corresponding expected output value generated by the safety-critical component operating in correct operating mode in response to the input value, the input value and expected output value comprising positioning data of the adjustment system;
check the safety-critical component in the test mode, the check comprising:
a calculation of a test output value based on the input value, the calculation of the test output value comprising:
check consistency of the input value, the check of the consistency of the input value comprising carrying out a checksum verification, the input value comprising axis-specific coordinates;
perform a forward transformation of the axis-specific coordinates into Cartesian coordinates;
conduct a first plausibility check, the conduction of the first plausibility check comprising comparing the Cartesian coordinates with predetermined Cartesian coordinates;
and
perform a consistency check or a second plausibility check of the transformed Cartesian coordinates, the performance of the consistency check or the second plausibility check comprising performing a check or checksum; and
a comparison of the test output value calculated in the test mode with the expected output value generated by the safety-critical component during the correct operating mode;
determine a deviation between the test output value and the expected output value determined in the test mode and determine whether the deviation exceeds a threshold; and
correct the regular operating mode, the correction comprising adjustment of the operation of the control motor of the robot system based on the deviation when the deviation exceeds the threshold.

21. A method for error recognition and correction in a control system of a medical treatment, diagnosis, or medical treatment and diagnosis device, the medical treatment, diagnosis, or medical treatment and diagnosis device comprising a robot system, the robot system comprising a control motor, the method comprising:
operating the medical treatment, diagnosis, or medical treatment and diagnosis device in a regular operating mode;
processing data in the regular operating mode;
instantiating a test mode of the control system, the test mode simulating real operation of the regular operating mode, the simulating comprising:
supplying a safety-critical component of the control system with test data of a test data record, the test data comprising pairs of previously determined values, the pairs of previously determined values comprising an input value that is occurrable as data in actual operation of the safety-critical component and a corresponding expected output value generated by the safety-critical component operating in correct operating mode in response to the input value, the input value and expected output value comprising positioning data;

checking, using a processor of the control system, the safety-critical component in the test mode, the checking comprising:

calculating a test output value based on the input value, the calculating comprising:

checking consistency of the input value, checking the consistency of the input value comprising carrying out a checksum verification, the input value comprising axis-specific coordinates;

performing a forward transformation of the axis-specific coordinates into Cartesian coordinates;

conducting a first plausibility check, the conducting of the first plausibility check comprising comparing the Cartesian coordinates with predetermined Cartesian coordinates; and performing a consistency check or a second plausibility check of the transformed Cartesian coordinates, the performing of the consistency check or the second plausibility check comprising performing a check or checksum; and comparing the test output value calculated in the test mode with the expected output value generated by the safety-critical component during the correct operating mode;

determining a deviation between the test output value and the expected output value determined in the test mode and determining whether the deviation exceeds a threshold; and correcting the regular operating mode, the correcting comprising adjusting the operation of the control motor of the robot system based on the deviation when the deviation exceeds the threshold, wherein the safety-critical component comprises a processing module, and wherein the transforming is by the processing module.

* * * * *